United States Patent [19]

Engelstad et al.

[11] Patent Number: 4,894,218

[45] Date of Patent: Jan. 16, 1990

[54] THERAPY AGENTS, METHODS OF PREPARATION, AND METHODS OF USE

[75] Inventors: Barry L. Engelstad, Orinda; David L. White, Oakland; John P. Huberty, Corte Madera, all of Calif.

[73] Assignee: Regents of the University of California, Oakland, Calif.

[21] Appl. No.: 200,476

[22] Filed: May 31, 1988

[51] Int. Cl.[4] ..................... A61K 43/00; C07C 129/12
[52] U.S. Cl. ...................................... 424/1.1; 564/237
[58] Field of Search .......................... 564/237; 424/1.1

[56] References Cited

U.S. PATENT DOCUMENTS

| | | | |
|---|---|---|---|
| 3,168,562 | 2/1965 | Walton et al. | 564/237 X |
| 4,584,187 | 4/1986 | Wieland et al. | 424/1.1 |
| 4,622,217 | 11/1986 | Wieland | 564/237 X |

*Primary Examiner*—John S. Maples
*Attorney, Agent, or Firm*—Townsend and Townsend

[57] ABSTRACT

New radiopharmaceutical compositions for use in nuclear medicine comprise radioastatinated benzylguanidine and radioastatinated carboxamidino phenylpiperazine. These compositions are used for treatment of disease, including neuroendocrine tumors, and specifically neuroblastoma.

4 Claims, 1 Drawing Sheet

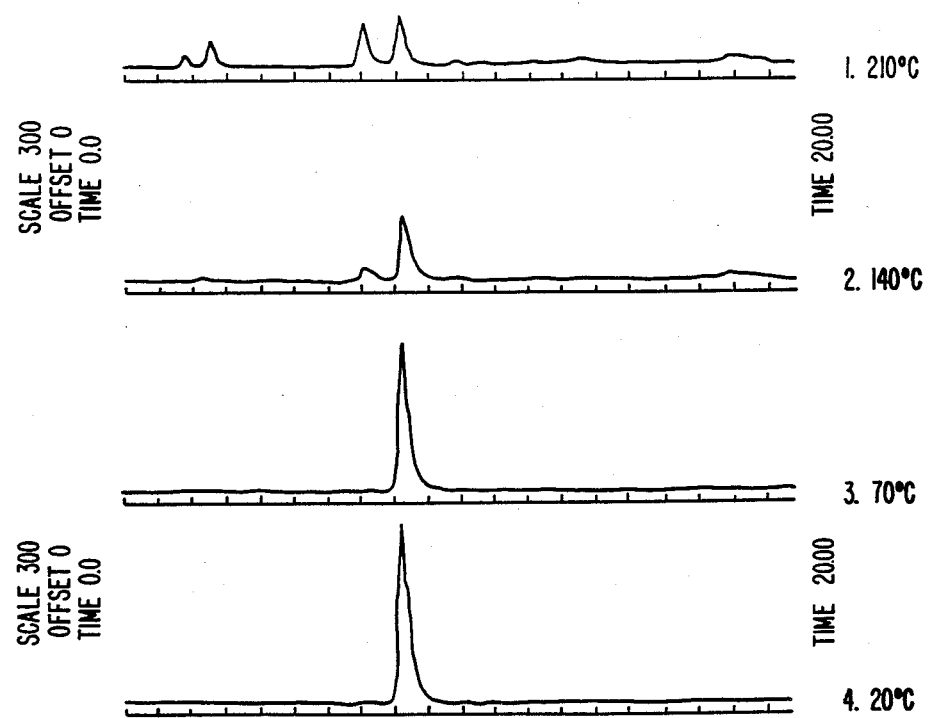
FIGURE

THERAPY AGENTS, METHODS OF PREPARATION, AND METHODS OF USE

BACKGROUND OF THE INVENTION

The present invention is directed to radioactive compounds useful for therapy.

Radionuclide therapy is the use of internally administered, unsealed pharmaceuticals whereby: sufficient radioactivity, in suitable composition, is administered to a patient; distribution of radioactivity occurs in vivo according to the route of administration and the biochemical properties of the radioactive drug; and internal irradiation occurs according to the pharmacologic fate and the physical decay properties of the radionuclide.

A limitation to radionuclide therapy is the requirement for selective toxicity: the benefit of injuring diseased tissue must exceed the risk of injuring healthy tissues. Many radioactive compounds are known, yet few yield selective toxicity sufficient to prove useful for radionuclide therapy. Therefore, a general need remains to discover additional or improved compounds so as to maximize irradiation of diseased tissue and to minimize irradiation of healthy tissue.

One basis for selective toxicity is in vivo localization: the chemical nature of the radioactive drug is preferred such that the radioactivity concentrates in diseased tissue. A variety of radio labeled compounds have been made that concentrate in diseased tissue, yet most disease-avid radioactive compounds concentrate insufficiently to prove suitable for radionuclide therapy. An example is $^{131}$I-albumin. Therefore, a specific need remains to discover additional or improved radioactive compounds that concentrate to a high degree in diseased tissue.

Another basis for selective toxicity is conferred by products of physical decay: emissions are preferred that deposit energy effectively in tissue. A variety of highly disease-avid radiopharmaceuticals are known, yet most emit decay products whose energy deposited in tissue is unsuitably concentrated for radionuclide therapy. Examples are radiopharmaceuticals labeled with $^{99m}$Tc, $^{67}$Ga, $^{111}$In, and $^{123}$I. Among types of emissions, irradiation is: poorly concentrated by uncharged, massless particles such as photons; better concentrated by charged, low mass particles, such as electrons; and best concentrated by charged, massive particles, such as alpha-particles. Therefore, a specific need remains to discover additional or improved radioactive compounds that abundantly emit electrons or alpha-particles.

Alpha-particle emitting pharmaceuticals have not been used for therapy of human diseases, except for rare examples of intracavitary use. Systemic use of alpha-emitting pharmaceuticals has been altogether unsuitable. Therefore, a general need remains to discover additional alpha-particle emitting pharmaceuticals suitable for therapeutic use in humans.

A limitation to using alpha-particle emitting pharmaceuticals for radionuclide therapy is the requirement for a short physical half-life and stable daughter radionuclide(s). As such, a large number of alpha-particle emitting radionuclides are known, but only two are suitable for use in radionuclide therapy: $^{212}$Bi and $^{211}$At. Of these, the 7 hour-life of $^{211}$At is more suitable for most radiopharmaceutical carriers. Therefore, a specific need remains to discover additional $^{211}$At-labeled pharmaceuticals suitable for human diseases.

A general limitation to medical therapy encompasses numerous diseases for which present therapy is limited or unsuitable. Various treatments, including combination of surgery, chemotherapy, immunotherapy or radiation therapy, are unsuitable for treatment of neuroendocrine tumors, a class of tumors sharing histological and biochemical features. For example, neuroblastoma, possibly the most common solid malignancy of childhood, is usually advanced at the time of diagnosis, such that 80–90% of children with the disease die within 1–2 years despite the best therapy available. Therefore, a general need remains to discover additional or improved therapies for neuroendocrine tumors, including neuroblastoma.

It is therefore the object of the present invention to provide alpha-emitting pharmaceuticals, which, are reliably safe and effective for therapy of neuroendocrine tumors, including neuroblastoma.

This and other objects will become apparent from the following description and claims.

BRIEF DESCRIPTION OF THE DRAWING

The FIGURE included herewith is a series of chromatograms relating to conditions involved in the preparation of one of the compounds of the present invention.

DESCRIPTION OF THE INVENTION

The compounds according to the present invention are of the following formulas.

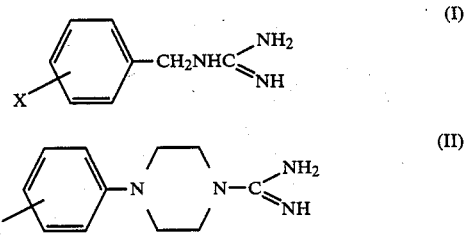

where X=$^{211}$At in any of ortho, meta or para positions.

While compounds according to the present invention having formula I or II might be prepared by halogen exchange or substitution by known electrophilic, nucleophilic or recoil astatination techniques (See Brown, I.: *Adv. Inorgan. Chem.* 1987; 31:43), it will be understood that the guanidine moiety in formula I or the carboxamidino moiety in formula II may undergo decomposition. The chemical lability of the guanidine or carboxamidino moieties requires avoidance of high temperature, strongly basic conditions or highly electrophilic reactants. $^{211}$At exchange or substitution reactions in the presence of such moieties are not known. As such, the compounds of the present invention must be prepared by methods heretofore untried.

Lacking any stable or long-lived astatine isotopes, organoastatine chemistry is incompletely understood and entails great difficulty. Identification of compounds by conventional techniques is made possible. In distinction to aryl halogenation with other halogens, many examples of astatination are known to be hindered by undefined impurities, unsuitable yields or unexpected side reactions (See Brown, I.: *Adv. Inorgan. Chem.* 1987; 31:43).

The compounds according to the present invention may be prepared by exchange halogenation with corresponding nonradioactive halogen substrates under suitable conditions. The unsubstituted or halogenated (F—, Cl—, Br—, I—) substrates corresponding to formula I or II may be prepared by any number of known routes. For example, general methods for synthesis of unlabeled guanidines include addition of amides to cyanamides and displacement of an alkylmercaptan by an amine from an alkylisothiouronium salt. Syntheses of the iodobenzylguanidines have been described (see Short, J.H. & Darby. T.D.: *J. Med. Chem.* 1967; 10:833) and are summarized:

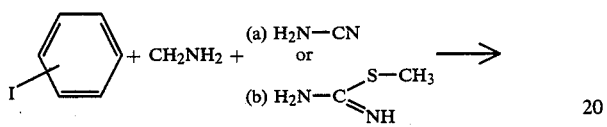

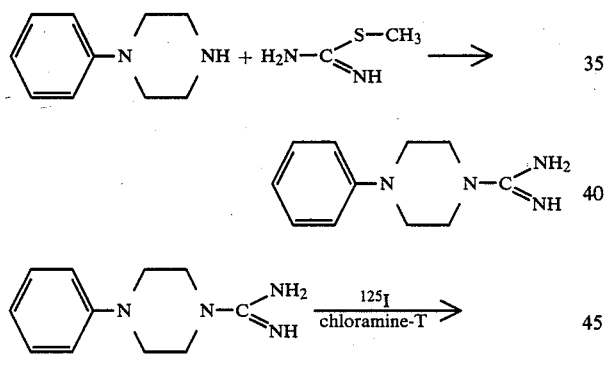

The preparation of 1-carboxamidino-4-(4iodo-phenyl)piperazine and its $^{125}$I analog have been described (see Hansen, R.N.: *Int. J. Nucl. Med. Biol.* 1983; 10:219) and summarized:

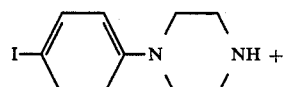

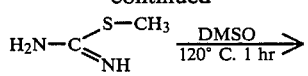

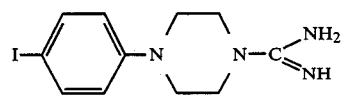

This preparative route, which is based on the electrophilic aromatic substitution of an aniline derivative, is suited essentially only for the para isomer, although small amounts of the ortho isomer may also be formed. The classical route to ortho- and meta- substituted products would involve reaction of the ortho- or meta-haloaniline with diethanolamine to form the corresponding 1-(2- or 3-halophenyl)piperazine (see Pollard. C. B. & Wicker, T. H.: *J. Am. Chem. Soc.* 1954; 76:1853):

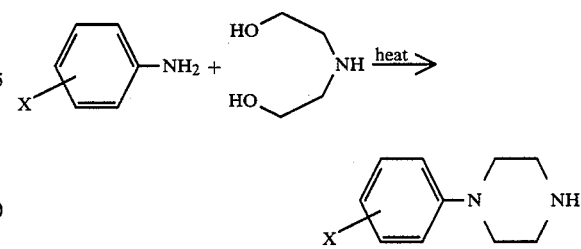

The piperazine would then be converted to the final product. An alternative route to (1-(2- and 3-bromophenyl)piperazines may occur ring closure with diethanolamine. The corresponding chloro compounds have been described (see Pollard CB & Wicker TH.: J Am Chem Soc 1954; 76:1853). The bromo compounds may be more stable toward thermal decomposition than the corresponding iodo compounds.

The astatination of the aromatic organic substrates herein described may be accomplished using one or more techniques in which exchange of $^{211}$At for another halogen is facilitated under suitable conditions.

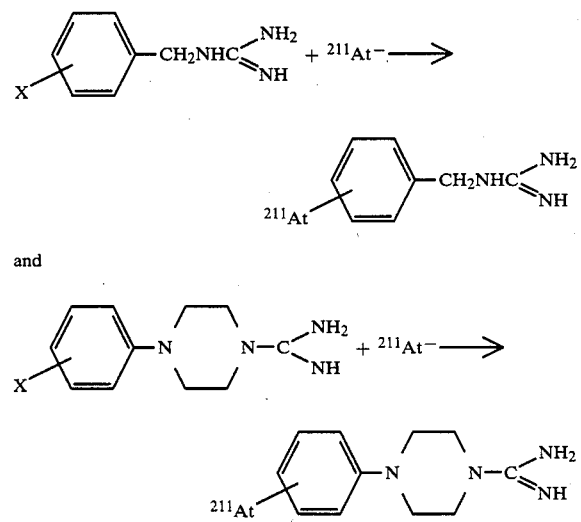

where X=F, Cl, Br, I

211At may be prepared by suitable alpha irradiation of a pure 209Bi target using standard cyclotron methods. The separation of 211At from the target may be accomplished by extraction or distillation. Distillation is preferred for compounds of the present invention so as to minimize impurities. Distillation may be accomplished by known methods (see Lambrecht, R. M., & Mirzadeh, S.: U.S. Pat. No. 4,681,727). A preferred method of distillation is to prepare a strongly oxidized gas phase, by using either $O_2$ or $O_3$, so as to minimize Bi or other impurities. The distilled 211At may be present in any of several oxidation states. At⁻ is preferred for suitable exchange reactions. Accordingly, a preferred reaction condition is to stabilize the 211At solution under a suitable reducing environment, such as $H_2S$ gas. The exchange with corresponding halogenated substrates (F⁻, Cl⁻, Br⁻ or I⁻) may be facilitated in the presence of n-butylamine. $(NH_4)_2SO_4$. $NH_4HSO_4$ or Cu(I). These methods entail less stringent reaction conditions than would other heretofore described 211At exchange or substitution methods and may advantageously permit exchange to occur without decomposition of the guanidine or carboxamidino moieties, a unique requirement of the compounds according to the present invention.

A particularly advantageous aspect of the present invention considers relative radiation response of diseased tissue: the use of radionuclide therapy is most suitable for disease conditions characterized by high natural sensitivity to radiation effects. Many diseases, including tumors, can be treated with suitable radionuclide therapy, yet few are distinguished by suitable radiosensitivity. An example is breast carcinoma, for which therapeutic radiopharmaceuticals are sought, yet which is inherently less radiosensitive than most tumors. The compounds according to the present invention are applicable for treatment of neuroblastoma, a tumor that is among the most radiosensitive diseases known. This is particularly advantageous in view of the clinical need for improved treatments of neuroblastoma.

Another particularly advantageous aspect of the present invention considers the range of effect of emissions: the distance, on a microscopic level, that charged particles deposit energy in tissue is preferred to reach the diseased cell's nucleus yet spare neighboring healthy cells. Electrons can be characterized by physical origin as beta particles, Auger electrons or conversion electrons. The electron range of effect is often unnecessarily long, as occurs with beta particles, or too short, as occurs with Auger or conversion electrons. An example is 131I-metaiodobenzylguanidine, a long range, beta-emitting, highly tumor-avid radiopharmaceutical which is unacceptably toxic, and has been lethal, due to bone marrow toxicity in children with neuroblastoma, a tumor that often infiltrates bone marrow. Being biogenic amine analogues, the compounds according to the present invention concentrate in peripheral portions of tumor cells. The emitted alpha-particles deposit intense energy over a range of effect, approximately 80 microns, intermediate to the unnecessarily long- or unacceptably short-range electrons described previously. This is particularly advantageous in view of the tumor radiobiology of neuroblastoma.

Another particularly advantageous aspect of the present invention considers the rate of tumor uptake in vivo and the physical half-life of 211At. In general tumor-seeking radiopharmaceuticals require time to concentrate in tumor, during which the decaying radionuclide is irradiating healthy tissues preferentially. The 7 hour half-life of 211At requires that tumor uptake of suitable 211At agents be rapid, that is, over minutes or hours. Yet other 211At-containing compounds, for example 211At-labeled antibodies, require much longer for maximal tumor uptake to occur. Being biogenic amine analogues, the compounds according to the present invention concentrate approximately 100–1000 time blood levels during the first few minutes after administration. This is particularly advantageous in view of the highly radiotoxic potential of 211At.

Another particularly advantageous aspect of the present invention considers the amount of 211At needed to treat systemic illness. In general amounts of 211At required (over 100 millicuries) for adult diseases, such as tumors, are far in excess of the amounts made (approximately 8-10 mCi) using best production methods. The compounds according to the present invention are most applicable for neuroblastoma, a disease of children, most of whom are under 4 years of age. Presently known 211At production methods enable sufficient amounts of 211At to be made to enable patients to be treated with neuroblastoma. This is particularly advantageous inasmuch as therapy with 211At could be made altogether feasible.

In general the compounds according to the present invention are generally useful to improve the treatment, by radionuclide therapy, of diseases of the body, through specific and nonspecific mechanisms of localization. Administration may be achieved by conventional means, such as, for example, intravenous, intraarterial, intralymphatic and intracavitary means.

Having described the preferred embodiments of the present invention, the following examples are presented for purposes of illustration, not by way of limitation.

EXAMPLES 1. 123I-metaiodobenzylguanidine and 131I-metaiodobenzylguanidine have been prepared and used by the inventors at the University of California San Francisco for clinical radionuclide imaging and therapy since 1981. Exchange iodination with nonradioactive metaiodobenzylguanidine has entailed either of two known methods: solid phase exchange facilitated with $NH_4SO_4$ (see Wieland, D. M., et al.: *J. Nucl. Med.* 1980: 21:349) or liquid phase exchange facilitated with Cu(I) (see Verbruggen, R. F., et al.: *Int. J. Rad. Appl. Instrum.* 1987; 38:303).

2. An experiment was performed to test the necessary stability of the guanidine moiety under conditions previously used (see Vasaros, L., et al.: *Radiochem. Radioanal. Lett.* 1981;47:313) for n-butylamine facilitated 211At exchange. The results are shown in the drawing which is an HPLC comparison of purified 123I-MIBG produced by the $(NH_4)_2SO_4$ process before and after incubation at various temperatures used for the n-butylamine reaction by Vasaros. et al. Column: polymeric reverse phase. Mobile phase: 25 mM formic acid in MeOH-$H_2O$. Gradient: 0 to 100% MeOH over 12 minutes. Flow-through UV and gamma detector in series.

What is claimed is:

1. A compound having the formula

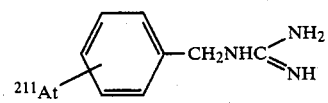

in which the position of the $^{211}$At atom is a member selected from the group consisting of ortho-, meta- and para-.

2. A compound in accordance with claim 1 in which the $^{211}$At atom is in the meta-position.

3. A method for the treatment of human diseases, said method comprising administering to humans afflicted by such diseases a compound having the formula

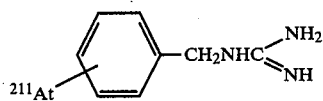

in which the position of the $^{211}$At atom is a member selected from the group consisting of ortho-, meta-, and para-, at a dosage rate of from about 1 mCi to about 200 mCi of radioactivity.

4. A method for the treatment of humans suffering from neuroendocrine tumors, said method comprising administering to said humans a compound having the formula

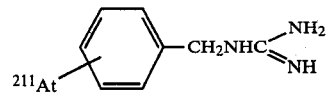

in which the position of the $^{211}$At atom is a member selected from the group consisting of ortho-, meta-, and para-, at a dosage rate of from about 1 mCi to about 200 mCi of radioactivity.

* * * * *